United States Patent
Hatlesad et al.

(10) Patent No.: US 6,949,075 B2
(45) Date of Patent: Sep. 27, 2005

(54) APPARATUS AND METHOD FOR DETECTING LUNG SOUNDS USING AN IMPLANTED DEVICE

(75) Inventors: John D. Hatlesad, Maplewood, MN (US); Quingsheng Zhu, Little Canada, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 119 days.

(21) Appl. No.: 10/331,175

(22) Filed: Dec. 27, 2002

(65) Prior Publication Data

US 2004/0127807 A1 Jul. 1, 2004

(51) Int. Cl.[7] .................................................. A61B 7/00
(52) U.S. Cl. ...................... 600/586; 600/529; 600/300; 607/9
(58) Field of Search ................................ 600/300, 301, 600/529–543, 586, 587, 595; 607/2, 5, 6, 9, 17, 18, 20

(56) References Cited

U.S. PATENT DOCUMENTS

| | | | |
|---|---|---|---|
| 4,519,395 A | | 5/1985 | Hrushesky |
| 4,930,517 A | | 6/1990 | Cohen et al. |
| 4,930,518 A | | 6/1990 | Hrushesky |
| 5,165,417 A | * | 11/1992 | Murphy, Jr. ................. 600/529 |
| 5,218,969 A | * | 6/1993 | Bredesen et al. ........... 600/523 |
| 5,584,868 A | | 12/1996 | Salo et al. |
| 5,928,156 A | * | 7/1999 | Krumbiegel et al. ........ 600/529 |
| 6,026,324 A | * | 2/2000 | Carlson ........................ 607/27 |
| 6,047,211 A | | 4/2000 | Swanson et al. |
| 6,116,241 A | * | 9/2000 | Huygen et al. ........ 128/204.23 |
| 6,139,505 A | * | 10/2000 | Murphy ....................... 600/532 |
| 6,145,183 A | | 11/2000 | Mauer |
| 6,168,568 B1 | * | 1/2001 | Gavriely ..................... 600/529 |
| 6,275,727 B1 | | 8/2001 | Hopper et al. |
| 6,409,675 B1 | * | 6/2002 | Turcott ....................... 600/508 |
| 6,456,256 B1 | | 9/2002 | Amundson et al. |
| 6,459,929 B1 | | 10/2002 | Hopper et al. |
| 6,480,733 B1 | * | 11/2002 | Turcott ....................... 600/516 |
| 2002/0151812 A1 | | 10/2002 | Scheiner et al. |
| 2002/0161412 A1 | | 10/2002 | Sun et al. |

OTHER PUBLICATIONS

Steven Lehrer, M.D., Understanding Lung Sounds, Second Ed., Copyright 1993, 1984 by W.B. Saunders Company, pp. 91–105.

J.P. Saul, R.J. Cohen, Respiratory Sinus Arrhythmia, Vagal Control of the Heart: Experimental Basis and Clinical Implications edited by M.N. Levy, P.J. Schwartz, copyright 1994, Futura Publishing Co., In., Armonk, NY, pp. 511–537.

M.R. Cowie, D.A. Wood, A.J.S. Coats, S.G. Thompson, V. Suresh, P.A. Poole–Wilson, G.C. Sutton, Survival of Patients with a New Diagnosis of Heart Failure: A Population Based Study, Heart 2000; 83:505–510.

* cited by examiner

*Primary Examiner*—Robert L. Nasser
*Assistant Examiner*—Pactricia Mallari
(74) *Attorney, Agent, or Firm*—Hollingsworth & Funk LLC

(57) ABSTRACT

Adventitious lung sounds indicative of lung congestion are detected using an implantable sensor. The sensor is adapted to be positioned adjacent to a pulmonary system and to output signals indicative of lung sounds in response to pulmonary system activity. A controller receives the signals and processes the signals to detect the presence of adventitious lung sounds. A respiratory cycle sensor operating in conjunction with the lung-sound sensor enables classification of an adventitious lung sound according to its time occurrence within the respiratory cycle. Posture sensing in conjunction with lung-sound sensing provides valuable additional information as to the severity of the lung congestion.

30 Claims, 5 Drawing Sheets

APPARATUS AND METHOD FOR DETECTING LUNG SOUNDS USING AN IMPLANTED DEVICE

BACKGROUND OF THE INVENTION

1. Field of the Invention

The invention relates generally to systems and methods for use in the treatment of congestive heart failure and, more particularly, to systems and methods for detecting adventitious lung sounds indicative of lung congestion.

2. Description of the Related Art

Cardiac pacemakers generally provide functions including sensing electrical signals generated by the heart, controlling stimulation of excitable tissues in the heart, sensing the response of the heart to such stimulation, and responding to inadequate or inappropriate stimulus or response, e.g., dysrhythmia, to deliver therapeutic stimuli to the heart. Some existing cardiac pacemakers also function to communicate with an external programmer device to support a variety of monitoring, diagnostic and configuration functions.

Certain cardiac pacemakers include an internal accelerometer for measuring the level of activity of the patient, e.g., movement caused by walking around. Such pacemakers process the accelerometer signals to reduce noise interfering with the measurement of the patient's activity, such as the sounds generated by the heart itself, and then use the processed signals as inputs to algorithms for generating the signals used to control the stimulation of the heart. For example, if accelerometer signals indicate that a patient is walking briskly, the pacemaker may stimulate the heart to beat at a faster rate, often subject to an upper rate limit, than when the patient is at rest.

Cardiac resynchronization therapy (CRT) is a relatively new but promising therapy for the treatment of congestive heart failure (CHF). In CRT, a cardiac pacemaker is implanted to restore synchrony to the beating of the heart, thereby increasing the heart's pumping efficiency.

CHF patients represent a large and growing population of patients that can benefit from implantable devices. CHF as a disease comprises a remarkably complicated set of inter-related systemic dysfunctions involving the cardiac and circulatory systems, the autonomic system, renal system, and the respiratory system. Due to the complex nature of CHF, in order to understand and track the progression of the disease, it is necessary to monitor a variety of symptoms presented by the affected systems.

One of the challenges of managing patients with CHF is to keep their lung congestion under control by adjusting the dosage of their diuretic medications. A sign of lung congestion at patient follow-up is the presence of adventitious lung sounds such as rales or crackles. Rales is an obvious crackling sound present upon auscultation of the chest. The presence of rales likely indicates the need to adjust the patient's diuretic regimen due to increased lung congestion. The worsening of lung congestion may in turn signify deterioration in the patient's underlying cardiac condition. In emergent CHF, the presence of rales is an independent indicator of mortality (Cowie, M. R. et al., "Survival of Patients with a New Diagnosis of Heart Failure: A Population Based Study," Heart 2000; 83:505:510).

Between follow up visits, the physician has no means of monitoring lung congestion other than relying on the patient to report relevant symptoms. Reliability of patient self-reporting of symptoms may vary considerably from patient to patient, with some patients either becoming unknowingly acclimated to the symptoms, or not wanting to bother their doctor by complaining about their symptoms.

Hence, those skilled in the art have recognized a need for an apparatus and method for monitoring a patient's pulmonary system for the presence of adventitious lung sounds, e.g., rales, indicative of lung congestion. The invention fulfills these needs and others.

SUMMARY OF THE INVENTION

Briefly, and in general terms, the invention is directed to systems and methods for detecting adventitious lung sounds indicative of lung congestion. In one aspect, the invention relates to a lung sound detection system that includes an implantable sensor and a controller. The sensor is adapted to be positioned adjacent to a pulmonary system and to output signals indicative of lung sounds in response to pulmonary system activity. The controller is adapted to receive the signals and to process the signals to detect the presence of adventitious lung sounds.

Since an adventitious lung sound, such as rales, is a distinctive, prominent crackling sound in auscultation, it follows that the sound propagates from the lungs through the intervening tissue and skin to the diaphragm of a stethoscope. Due to the location of implantable device, such as pulse generators, the sensor, e.g., an accelerometer, mounted on or in an implanted pulse generator picks up lung sounds. Due to the prominent and distinctive nature of the adventitious lung sounds, it is possible to reliably detect the presence of such sounds on a continuous basis in an ambulatory patient.

A respiration sensor operating in conjunction with a lung-sound sensor enables classification of an adventitious lung sound according to its time occurrence within the respiratory cycle. Accordingly, in a detailed facet, the system includes a respiratory sensor adapted to output signals indicative of the respiratory cycle associated with the pulmonary system. For a specific type of adventitious lung sound, monitoring the respiratory cycle allows for a narrowing of the search window within the respiratory cycle to improve reliability of detection by reducing false detections. Thus, in a further detailed aspect, the controller is adapted to receive the respiratory-cycle signals, to detect portions of the respiratory cycle based on the respiratory-cycle signals and to process lung-sound signals only during specific portions of the respiratory cycle.

In clinical texts and tutorials on auscultation, the adventitious lung sound known as rales is subdivided primarily in two clinically significant ways. One of these divides rales into categories based on when the sound occurs within the respiratory cycle. For example the most common type is "late inspiratory" rales, versus "early inspiratory" or "expiratory" rales. Accordingly, the controller is further adapted to process the lung-sound signals only during the inspiratory portion and to detect early and late portions of the inspiratory portion.

The other way of subdividing rales is by the quality of the sound itself, being typically divided into "fine" versus "coarse" rales. Digital signal processing of the rales sound waveform may be used to distinguish between these different types of rales signatures, thus classifying rales by sound quality.

In some patients, congestion is only a problem when they lie down (orthopnea). In these patients, lung congestion may develop as they sleep, and may resolve itself when they remain upright, so that rales never presents at clinic follow-ups. Indeed the presence of rales regardless of posture is a sign of the severity of the congestion. Accordingly, posture sensing in conjunction with rales sensing provides valuable additional information as to the severity of the lung congestion. Thus, in another aspect, the implantable sensor is further adapted to output signals indicative of the posture of the body associated with the pulmonary system, and the controller is further adapted to receive the signals and to process the signals to detect the posture of the body. Due to its continuous, ambulatory nature, the system is able to identify and trend the incidence of nighttime adventitious lung sounds that would otherwise go undetected Significant changes in adventitious lung sound trends may portend incidents of CHF exacerbation. In a remote patient management system, trending the incidence of adventitious lung sounds may provide valuable information to alert the patient to contact the physician's office or to alert the physician's office directly of a possible onset of CHF exacerbation.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
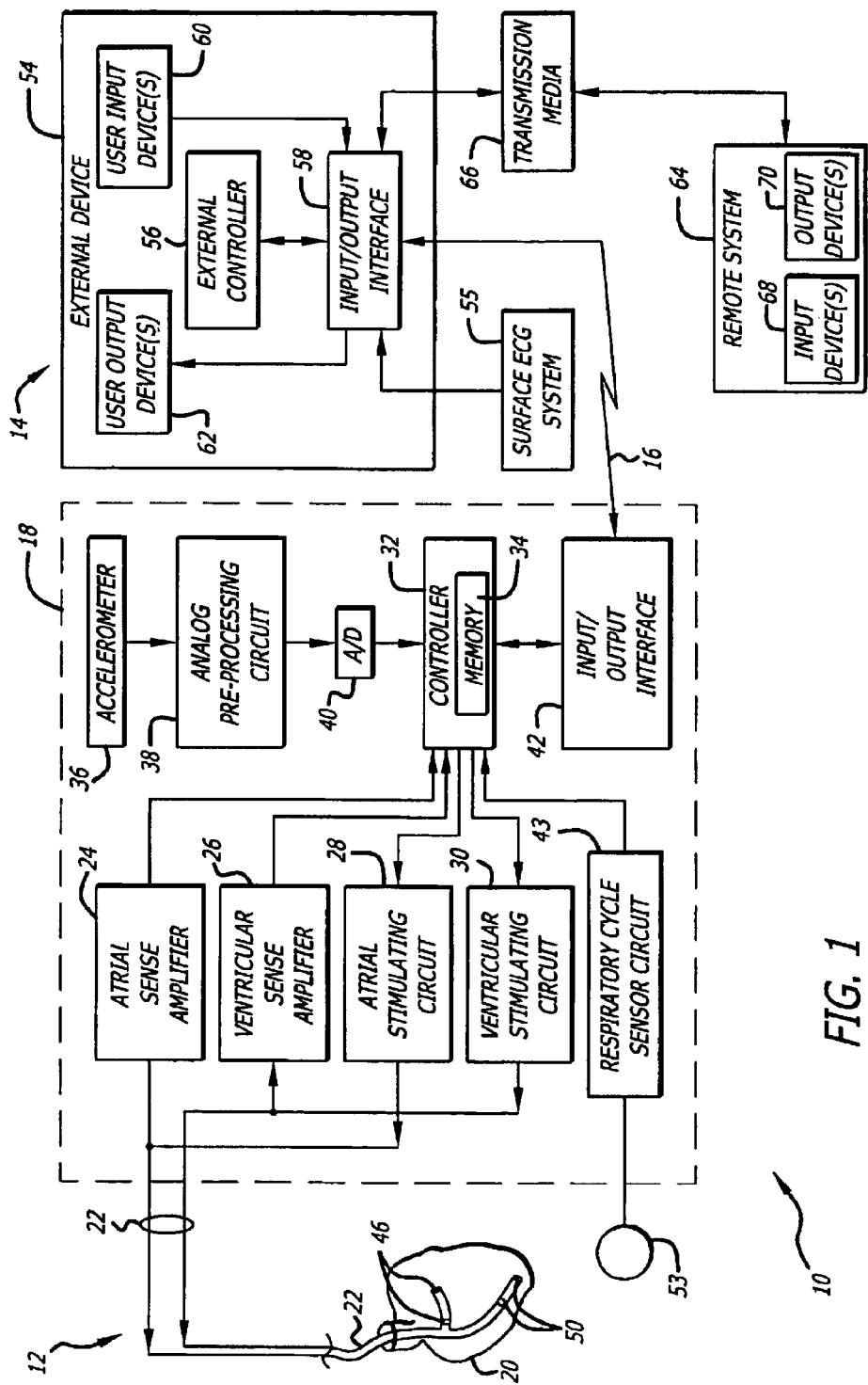
FIG. 1 is a block diagram of an exemplary system for detecting lung sounds and respiratory cycles using an implantable sensor.

Referring to FIG. 1, an exemplary system 10 for use in the detection of adventitious lung sounds indicative of pulmonary congestion comprises an implantable system 12 and an external system 14. The implantable system 12 and the external system 14 are configured to communicate via a communications link 16. In one embodiment, link 16 uses radio-frequency (RF) signals. In another embodiment, the link 16 uses inductive signals. These communications may support monitoring, diagnostic and configuration functions.

The implantable system 12 includes an implantable device 18 operatively coupled to a patient's heart 20 by one or more pacing leads 22. The components of the implantable device 18 may include an atrial sense amplifier 24, a ventricular sense amplifier 26, an atrial stimulating circuit 28, a ventricular stimulating circuit 30, a controller 32, a memory 34, an accelerometer 36, an analog pre-processing circuit 38, an analog-to-digital (A/D) converter 40, an input/output (I/O) interface 42 and a respiratory cycle sensor circuit 43. The components of the implantable device 18 are housed within an implantable housing (indicated by the broken lined box in FIG. 1.) which is implanted in the area of the patient's chest, e.g., in the pectoral region.

The atrial sense amplifier 24, ventricular sense amplifier 26, atrial stimulating circuit 28 and ventricular stimulating circuit 30 are operatively coupled to the pacing leads 22. The pacing leads 22 include an atrial electrode or electrode pair 46 adapted to be disposed in the right atrial chamber of heart 20, and a ventricular electrode or electrode pair 50 adapted to be disposed in the right ventricular chamber of heart 20. Sensed atrial and ventricular electrical signals generated by the electrodes 46 and 50 are applied to the atrial and ventricular sense amplifiers 24 and 26, respectively, and atrial and ventricular stimulating signals generated by the atrial and ventricular stimulating circuits 28 and 30 are applied to the atrial and ventricular electrodes 46 and 50, respectively. The atrial sense amplifier 24, ventricular sense amplifier 26, atrial stimulating circuit 28, and ventricular stimulating circuit 30, are each also operatively coupled to the controller 32.

An indifferent electrode 53 is disposed on the housing of the implantable device 18. The indifferent electrode 53 may be used in conjunction with an electrode within the heart 20, for example, the ventricular electrode 50, to provide periodic transthoracic impedance measurements. These measurements are applied to the respiratory cycle sensor circuit 43 where they are processed using techniques known in the art. The processed signals are provided to the controller 32, which as described later, uses the signals to monitor the respiratory cycle of the patient. The indifferent electrode 53, the ventricular electrode 50 and the respiratory cycle sensor circuit 43 function as a respiratory cycle sensor.

The controller 32 includes a micro-controller or microprocessor which is configured to execute a program stored in a read-only memory (ROM) portion of the memory 34, and to read and write data to and from a random access memory (RAM) portion of the memory 34. By executing the program stored in the memory 34, the controller 32 is configured to process the atrial and ventricular electrical signals from the atrial and ventricular sense amplifiers 24 and 26, and to provide control signals to the atrial and ventricular stimulating circuits 28 and 30. In response, the stimulating circuits 28, 30 provide stimulating pulses to the heart 20 via the atrial and ventricular electrodes 46, 50 at appropriate times. The stimulating circuits 28, 30 function as a pulse generator. In other embodiments, the controller 32 may include other types of control logic elements or circuitry. The controller 32 is also programmed to process the data received from the accelerometer 36 and respiratory cycle sensor circuit 43 to monitor the activity of the patient's pulmonary system.

The implantable device 18 may be referred to as a dual-chamber pacemaker since pacemaking functions are provided to both atrial and ventricular chambers of the heart 20. In another embodiment, sensing and/or stimulating is additionally provided to the left ventricle to provide cardiac resynchronization therapy. In another embodiment, the implantable system includes a single-chamber pacemaker that senses electrical signals and provides stimulating pulses to a single chamber of heart 20. In yet another embodiment, the implantable system does not provide any sensing electrodes for sensing any cardiac electrical signals, but is configured to sense and transmit signals representing pulmonary system activity, e.g., lung sounds, using a sensor such as accelerometer 36, as described below.

The accelerometer 36 is configured to provide sensed vibratory signals to the analog pre-processing circuit 38, which generates an analog output signal which is digitized by the A/D converter 40. The digitized accelerometer signal is received by the controller 32. In the embodiment of FIG. 1, the accelerometer 36 is located internally to the housing of the implantable device 18. In another embodiment, the accelerometer 36 is located externally to the implantable housing. The accelerometer 36 may include, for example, a piezo-electric crystal accelerometer sensor of the type used by pacemakers to sense the activity of the patient, or may include other types of accelerometers that are packaged to fit in the implantable housing. Depending on its sensitivity, frequency response and configuration, the accelerometer 36 may detect vibrations from a variety of sources, including the heart, lungs, patient activity and patient posture. Alternatively, patient posture may be detected using devices other than an accelerometer, such as a tilt switch. To detect lung sounds, other types of sound-detecting sensors or microphones may also be used in addition to the piezo-electric crystal accelerometer sensors, such as pressure sensors or vibration sensors configured to respond to sounds made by the pulmonary system.

In another embodiment, the system 10 includes a plurality of sound-detecting sensors. In this embodiment, the plurality of sensed lung sound signals from the plurality of sensors may be individually transmitted to the external system 14 for display as individual traces, may be combined, e.g., averaged, by the external system 14 before being displayed as a single trace, or may be combined by the controller 32 before being transmitted to the external system 14 as a single lung sound signal. Alternatively, the controller 32 may process the plurality of sensor signals to make an assessment of the type, degree and/or severity of adventitious lung sounds, and store one or more of such assessments in memory 34, or transmit them to the external system 14. These sensors may include different types of sensors, sensors that are located in different locations, or sensors that generate sensed signals which receive different forms of signal processing.

In one embodiment, the accelerometer 36 is configured to detect sensed signals representative of two distinct physical parameters: (1) the posture of the patient, and (2) the lung sounds generated by the pulmonary system. Accordingly, analog pre-processing circuit 38 is configured to pre-process the sensed signals from accelerometer 36 in a manner which conforms to the signal characteristics of both of these physical parameters. For example, if the frequencies of interest for measuring the patient's posture are below 1 Hz, while the frequencies of interest for detecting adventitious lung sounds are above 200 Hz, then the analog pre-processing circuit 38 may include two filters. One filter would be a low-pass filter having a cutoff frequency of 1 Hz for obtaining posture-sensing related signals. The second filter would be a high-pass filter having a cut-off frequency of approximately 200 Hz for obtaining adventitious lung-sound related signals. Along with filtering, the analog pre-processing circuit 38 may perform other processing functions including automatic gain control (AGC) functions. These signal processing functions could also be performed by the external system 14. The cut-off frequencies mentioned above are merely exemplary and may vary.

In another embodiment, the implantable device 18 has two pre-processing channels for receiving sensed signals from the accelerometer 36. In still another embodiment, the implantable device 18 includes two accelerometers, with one accelerometer configured to generate sensed signals representative of the posture of the patient and the other accelerometer configured to generate sensed signals representative of lung sounds. In these latter two embodiments, any hardware and/or software processing performed on the sensed signals can conform to the specific characteristics of the respective sensed signals. For example, the analog pre-processing circuit used for the posture sensed signals can provide a low-pass filter with a cutoff frequency of 1 Hz, while the analog preprocessing circuit for the lung-sound sensed signals can provide a high-pass filter with a cutoff frequence of 200 Hz. In the latter case, each accelerometer 36 can be selected, located and/or oriented to maximize the detection of the respective physical parameter. In yet another embodiment, if the implantable device 18 does not need to sense the posture of the patient, accelerometer 36 may measure only the sounds made by the pulmonary system 20, or may measure both lung sounds and activity.

The controller 32 is capable of bi-directional communications with the external system 14 via the I/O interface 42. In one embodiment, the I/O interface 42 communicates using RF signals. In other embodiments, the I/O interface 42 communicates using inductive signals, or a combination of RF and inductive signals, e.g., RF signals for receiving data from the external system 14 and inductive signals for transmitting data to the external system, or vice-versa. The controller 32 uses the I/O interface 42 for bi-directional communications with the external system 14 to support conventional monitoring, diagnostic and pacemaker configuration functions. The controller 32 also uses the I/O interface 42 to telemeter data representative of the lung-sound related signals and posture related signals sensed by the accelerometer 36 and respiratory cycle related signals sensed by the respiratory cycle sensor circuit 43 to the external system 14. Such data may consist of raw or processed waveforms, or of descriptive assessments of the patient's lung sounds and/or other heath related parameters.

In various embodiments, the controller 32 further uses the I/O interface 42 to telemeter data representative of cardiac electrical signals, i.e., electrogram or EGM signals, which may include data representative of atrial electrical signals, i.e., A EGM signals sensed by the atrial electrode 46, and/or data representative of ventricular electrical signals, i.e., V EGM signals sensed by the ventricular electrode 50. Thus, the implantable system 12 is capable of sensing lung sounds, patient posture, patient activity, respiratory cycle, atrial electrical signals and ventricular electrical signals, and of telemetering data representative of the lung sounds, activity, posture, respiratory cycle and/or cardiac electrical signals to the external system 14.

In one embodiment, the external system 14 includes an external device 54 and a surface electrocardiograph (ECG) system 55. The external device 54 includes an external controller 56, an I/O interface 58, user input device(s) 60, and user output device(s) 62. Using the I/O interface 58, the external controller 56 is configured for bi-directional communications with the implantable device 18, for receiving input signals from the input device(s) 60, and for applying control signals to the output device(s) 62. The input device (s) 60 include at least one input device which allows a user to generate input signals to control the operation of the external device 54, such as at least one user-actuatable switch, knob, keyboard, pointing device, touch-screen, voice-recognition circuit, etc. The output device(s) 62 include at least one display device, e.g., CRT, flat-panel display, etc., an audio device, e.g., speaker, headphone, or other output device which generates user-perceivable outputs, e.g., visual displays, sounds, etc., in response to control signals. The external controller 56 is configured to receive the data representative of lung sounds, patient activity, posture, respiratory cycle, atrial electrical signals and/or ventricular electrical signals from implantable system 18, and to generate control signals that, when applied to the output device(s) 62, cause the output device(s) to generate outputs that are representative of the lung sounds, patient posture, respiratory cycle, the atrial electrical signals and/or the ventricular electrical signals.

In one embodiment, the external device 54 comprises an external programming device for a cardiac pacemaker, such as the ZOOM™ external programmer available from the Guidant Corporation, except that the external programmer is configured, i.e., programmed or otherwise set up, to perform the various functions described in the present application.

In one embodiment, system 10 further includes a remote system 64 operatively coupled to communicate with external system 14 via transmission media 66. Remote system 64 includes one or more user input device(s) 68, and one or more user output device(s) 70, which allow a remote user to interact with remote system 64. Transmission media 66 includes, for example, a telephone line, electrical or optical cable, RF interface, satellite link, local area network (LAN), wide area network (WAN) such as the Internet, etc. The remote system 64 cooperates with the external system 14 to allow a user located at a remote location to perform all or a subset of the diagnostic or monitoring functions that may be performed by a user located at the external system 14. For example, data representative of lung sounds, patient posture, respiratory cycle and/or cardiac electrical signals are communicated by the external system 14 to the remote system 64 via the transmission media 66 to provide a visual display and/or an audio output on the output device(s) 70, thereby allowing a physician at the remote location to aid in the diagnosis of a patient. The system 64 is "remote" in the sense that a user of the remote system is not physically capable of actuating the input device(s) 60 and/or of directly perceiving outputs generated by the output device(s) 62. For example, the remote system 64 may be located in another room, another floor, another building, another city or other geographic entity, etc., from the external system 14.

Figure 2:
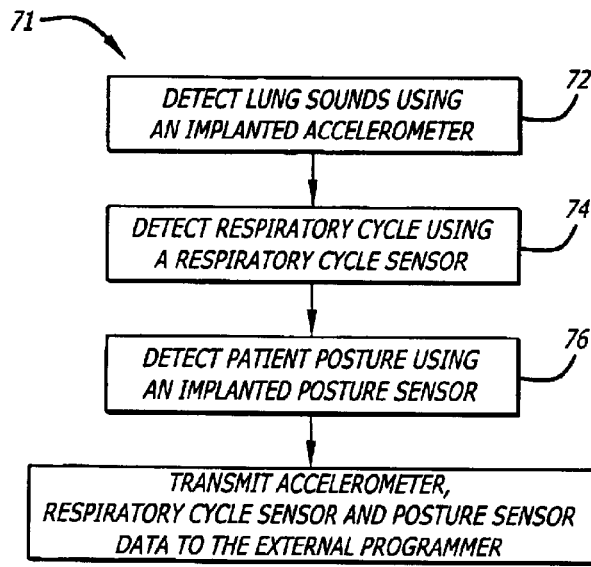
FIG. 2 is a flow chart illustrating one embodiment of the processing performed by the controller of the system of FIG. 1.

Referring to FIG. 2, in one embodiment, the processing 71 performed by the controller 32 of the implantable device 18 includes detecting lung sounds by receiving sensed signals representative of the lung sounds from the accelerometer 36 (at 72), detecting the respiratory cycle by receiving sensed signals representative of the respiratory cycle from the respiratory cycle sensor circuit 43 (at 74), detecting patient posture by receiving sensed signals representative of posture from a posture sensor (at 76). In one configuration, the accelerometer 36 functions as the posture sensor. In another embodiment, a tilt switch (not shown) functions as the posture sensor. In the accelerometer 36 configuration, the accelerometer is implanted with a sensitive axis along the patient's inferior-superior axis. Positioned as such, the accelerometer 36 senses the force of gravity when the patient is upright, thus producing an output above a certain threshold. When the patient is recumbent, the force of gravity is generally perpendicular to the sensitive axis of the accelerometer and the accelerometer does not sense as much gravitational force, thus the output produced is below the threshold. In the tilt switch configuration, the posture is determined by whether the switch is opened, which is typically indicative of recumbent posture, or closed, which is typically indicative of upright posture. The processing 71 further includes transmitting data representative of the lung sound, patient posture and respiratory cycle signals to the external device 54 (at 78). This data is obtained by digitizing the sensed signals.

In another embodiment, the processing 71 further includes signal processing the accelerometer signal (either one or both of lung sound and patient posture), respiratory cycle sensor circuit signals and patient posture signals to generate processed sensed signals (between 76 and 78), and then transmitting the processed sensed signals to the external device 54 (at 78). The signal processing may also be performed on only one or two of these sensed signals. Performing the signal processing in implantable device 18 may increase the computational requirements for the implantable device 18 but may decrease storage requirements for the implantable device while it is out of communication with the external device 54, and may also decrease the transmission load between the implantable device and the external device. It is to be understood that the division of signal processing between the implantable device 18 and external device 54 could be modified from that disclosed herein, as would be apparent to a person of skill in the art. In an alternate configuration, the signal processing may be performed in the external device 54. In another embodiment, the processing 71 also includes storing one or more of the raw or processed sensed signals in the memory 34 for later retrieval by the external device 54.

Figure 3:
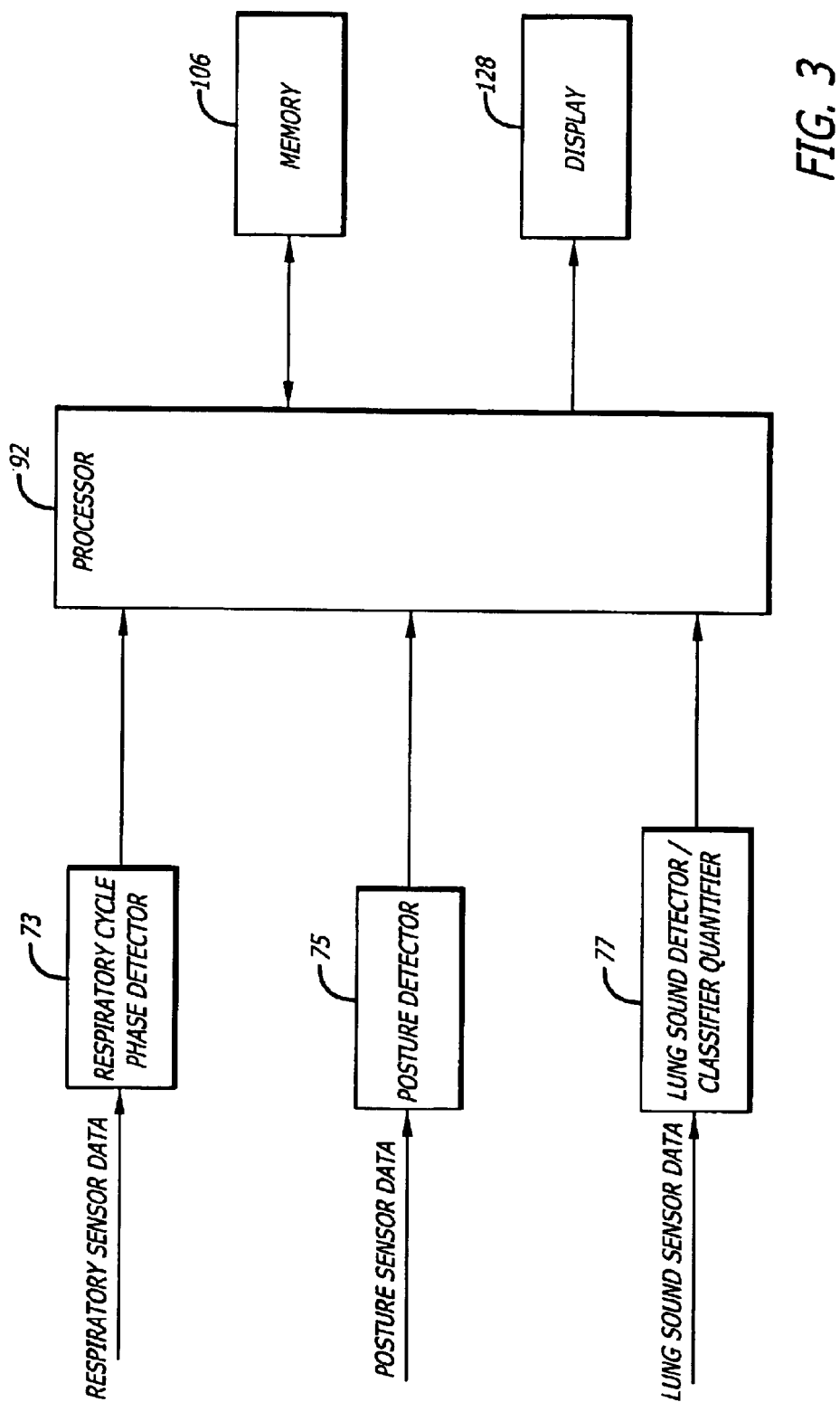
FIG. 3 is a block diagram of an exemplary system for performing the processing of FIG. 2 including a respiratory cycle phase detector, a posture detector and a lung sound detector/classifier/quantifier.

With reference to FIG. 3, the controller 32 includes a respiratory cycle phase detector 73 configured to detect the inspiratory and expiratory phases of the patient's respiratory cycle using respiratory sensor data provided by the respiratory cycle sensor. The controller 32 also includes a posture detector 75 configured to detect the posture of the patient using posture sensor data provided by an accelerometer or other posture sensor, e.g., tilt switch. The controller 32 further includes a lung sound detector/classifier/quantifier 77 configured to detect adventitious lung sounds using lung sound sensor data provided by an accelerometer or other sound sensor. Details of the operation of the respiratory cycle phase detector 73, posture detector 75 and lung sound detector/classifier/quantifier 77 are provided below.

Figure 4:
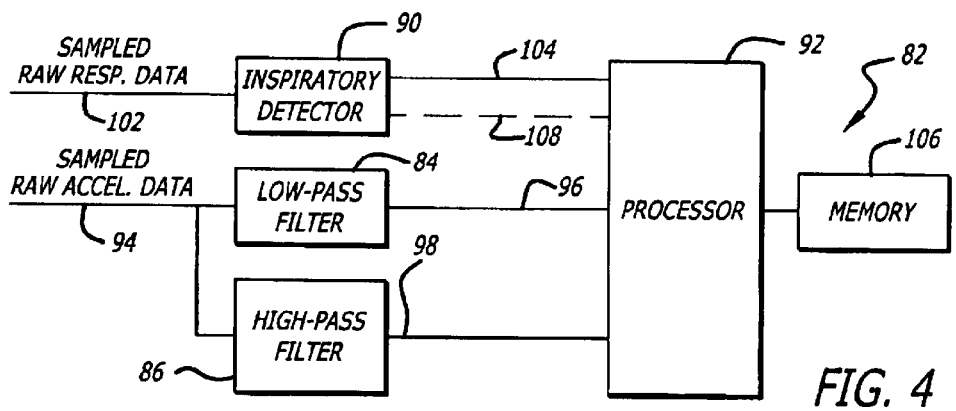
FIG. 4 is a block diagram illustrating one embodiment of the processing performed on the lung-sound and respiratory-cycle signals provided by the system of FIG. 1.
Figure 5:
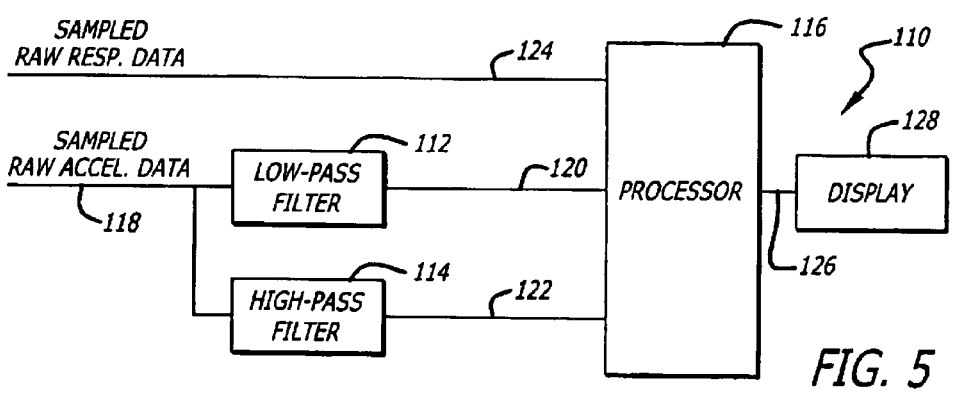
FIG. 5 is a block diagram illustrating another embodiment of the processing performed on the lung-sound and respiratory-cycle signals provided by the system of FIG. 1.

Referring to FIGS. 4 and 5, the signal processing performed on the accelerometer data and respiratory cycle sensor data by the internal controller 32 or the external controller 56 in accordance with one embodiment of the invention is shown. In other embodiments, some or all of this signal processing could instead be performed by the controller 32 of implantable device 18, or by either the external or implantable hardware. Signal processing includes a first processing path 82 (FIG. 4) used for machine detection of adventitious lung sounds, such as "rales." As previously described, rales is an obvious crackling sound present upon auscultation of the chest and is an indication of lung congestion. A second processing path 110 (FIG. 5) provides for visual display of lung sounds in conjunction with the respiratory cycle, is described later with reference to FIG. 5. Alternatively, only one of the signal processing paths 82 and 110 may be provided.

The first processing path 82 includes a low-pass filter 84, a high-pass filter 86, an inspiratory detector 90 and a processor 92. Raw accelerometer data 94 (representative of the lung sounds and posture) is applied to the low-pass filter 84, which has a cutoff frequency set to pass only data representative of sensed signals having frequencies indicative of patient posture, to produce remaining low-pass filtered data 96. In one example, the cutoff frequency is 1 Hz.

The accelerometer data 94 is also applied to the high-pass filter 86, which has a cutoff frequency set to pass only that data representative of sensed signals having frequencies indicative of lung sounds, to produce remaining high-pass filtered data 98. In one example, the cutoff frequency is 200 Hz, such that normal breath sounds, heart sounds, patient activity and posture signals are attenuated, but adventitious lung sounds, such as crackles are passed through. The cutoff frequency of the high-pass filter 86 is also set to reject frequencies due to movement of the patient, e.g., walking around, muscle twitches, etc., to the extent that the lung sound signals still pass.

Low-pass filtered data 96 and high-pass filtered data 98 are applied to the processor 92 for processing. In one configuration, this processing involves comparing a characteristic of the sound signal represented by the high-pass filtered data 98 to a criteria indicative of adventitious lung sounds. For example, the signal characteristic may be the signal amplitude while the criteria indicative of adventitious lung sounds maybe an amplitude threshold value. If the amplitude of the sound signal exceeds the threshold, adventitious lung sounds are present and the processor 92 records the time of day along with the high-pass filtered data 98 to memory 106.

The processor 92 may also further process the high-pass filtered data 98 to determine the type and/or severity of the adventitious lung sounds. For example, once the presence of an adventitious lung sounds is detected, the filtered data 98 indicative of the sounds may be compared to other criteria to provide an indication of the severity of the condition associated with adventitious lung sounds, e.g., lung congestion. This criteria may include anyone of a plurality of increasing amplitude levels. The severity of the condition may be determined based on the amplitudes of the adventitious lung sounds relative to the criteria amplitudes, with a higher amplitudes being indicative of increased condition severity. Alternatively, or additionally, the criteria may be time based, in which case the processor determines the amount of time that adventitious lung sounds are present. The severity of the condition associated with the adventitious lung sounds would be determined based on the time duration of lung sound, with a longer duration being indicative of increased severity. For example, the continuous presence of adventitious lung sounds for a time duration of 12 hours would be considered more severe than a continuous presence for 4 hours.

The processor 92 also receives the low-pass filtered data 96 related to patient posture data. If adventitious lung sounds are present, the processor 92 may analyze the posture data 96 to determine whether the patient is upright or recumbent. This is done by comparing the posture data 96 to a criteria indicative of a specific posture. For example, if the posture data is indicative of an accelerometer output above a threshold value associated with upright posture, the patient's posture is determined to be upright. Conversely, if the accelerometer output is below the threshold, the patient's posture is determined to be recumbent. The posture data 96 is recorded in memory 106 along with the adventitious lung sound data 98. If the processor 92 does not detect adventitious lung sounds, nothing is recorded in the memory 106 or a value indicative of the absence of such sounds is recorded.

Since adventitious lung sounds are most commonly present only during the inspiratory portion of the respiratory cycle, the controller 56 may be further configured to monitor for such sounds only during the inspiratory portion. As a result, the possibility of false detection of rates is reduced. In this configuration, raw respiratory cycle sensor data 102 (representative of the respiratory cycle) is applied to the inspiratory detector 90. The inspiratory detector 90 is programmed to identify specific trends in the sensor data 102 as being indicative of the inspiratory portion of the respiratory cycle. Examples of such trends are described further below. When an inspiratory portion is detected, the detector 90 outputs a trigger signal 104 to the processor 92. This trigger 104 opens a window of interest that coincides with the inspiratory portion of the respiratory cycle. When triggered, the processor 92 processes the high-pass filtered data 98 to determine if adventitious lung sounds are present in the same manner as previously described.

In an alternate configuration, the high-pass filter 86 is followed with a spectrum analyzer, which processes the output of the high-pass filter 98 and represents the spectral or frequency content of the data as a function of intensity. In this configuration, the processor 92 processes the output of the spectrum analyzer to determine if adventitious lung sounds are present. This processing involves comparing the intensities of those spectral or frequency components within the spectrum that are greater than a specified frequency, for example, 200 Hz, to a threshold value indicative of adventitious lung sounds. If the intensity of the components exceeds the threshold, adventitious lung sounds are present and the processor 92 records the data to memory 106 along with the posture of the patient. The output of the spectrum analyzer may further be used to distinguish between different types of adventitious lung sounds, e.g., between coarse and fine crackles. The severity of the adventitious lung sounds may be determined based on additional analysis involving different threshold intensities and time durations, similar to that previously described.

Figure 6:
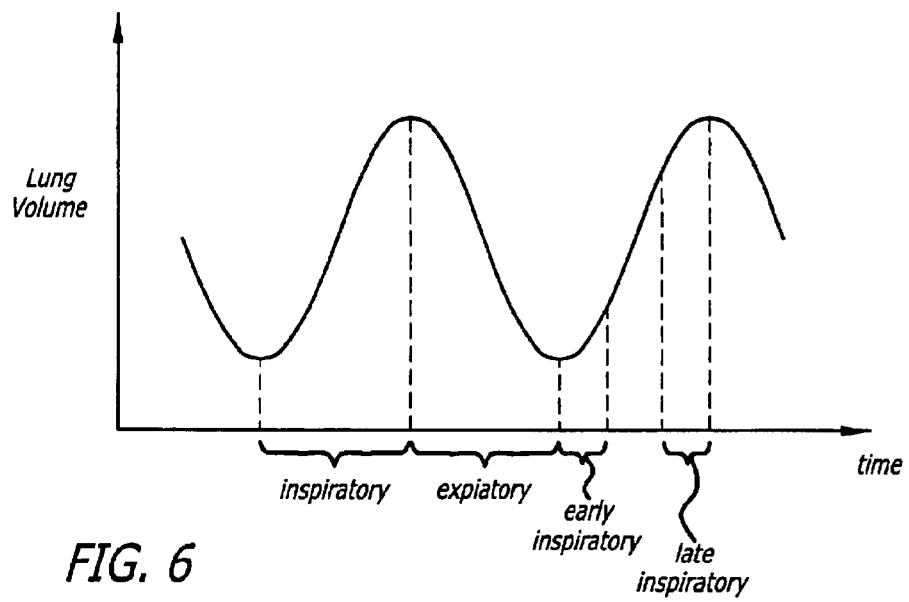
FIG. 6 is a waveform representative of lung volume verses time for a respiratory cycle.
Figure 7:
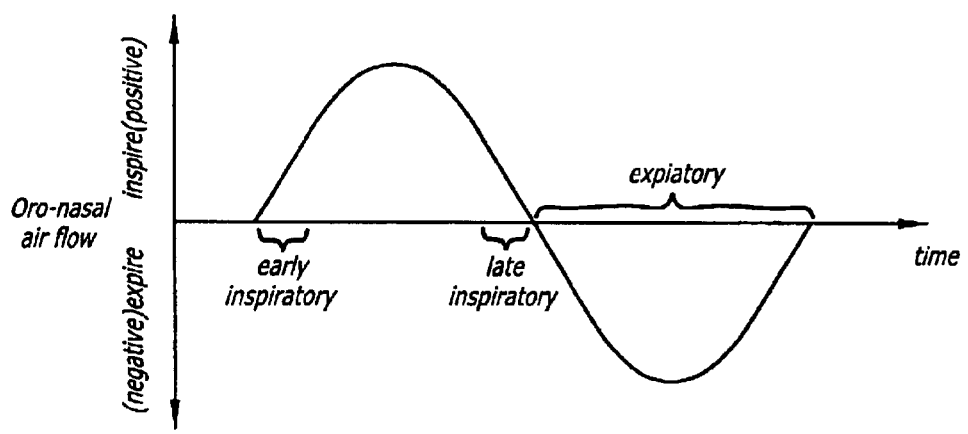
FIG. 7 is a waveform representative of air flow verses time for a respiratory cycle.

If adventitious lung sounds are detected, the processor 92 may be further configured to identify the presence of early-inspiratory adventitious lung sounds, late-inspiratory adventitious lung sounds or expiratory adventitious lung sounds. In this configuration, in addition to the trigger signal 104, the processor 92 also receives the respiratory-cycle data 108 associated with the inspiratory portion. The processor 92 monitors this data to identify the early and late parts of the inspiratory portion. In one configuration, the processor 92 may be programmed to identify specific data patterns as being indicative of early-inspiratory or late-inspiratory. For example, with reference to FIG. 6, if the data is representative of lung volume and these values reach a minimum value, then begin to display an upward trend, i.e., increase in value, over time, then the respiratory cycle is likely in its early-inspiratory portion. Conversely, if the lung volume values continue an upward trend over time then reach a maximum value after which they begin to decrease, then the end of the upward trend represents the late-inspiratory portion of the respiratory cycle. With reference to FIG. 7, if the data is representative of air flow and these values are positive and display an upward trend, i.e., increase in value, over time, then the respiratory cycle is likely in its early-inspiratory portion. Conversely, if the air flow values are positive and display a downward trend, i.e., decrease in value, over time then the respiratory cycle is likely in its late-inspiratory portion.

With reference to FIG. 5, the second processing path 110 includes a low-pass filter 112, a high-pass filter 114 and a processor 116. Raw accelerometer data 118 (representative of the lung sounds and patient posture) is applied to the low-pass filter 112 to provide data indicative of patient posture 120 and the high-pass filter 114 to provide data indicative of lung sounds 122, in the same manner as previously described with respect to the first processing path 82. The posture data 120 and lung sound data 122, along with the raw respiratory cycle sensor data 124, are applied to the processor 116. The data 120, 122, 124 is then further processed using techniques known in the art to output display data 126 to a display 128. The display 128 provides a visual display of the lung sound data, respiratory cycle data and posture data which may be useful to a physician, nurse, medical technician or other user of system 10.

The signal processing for the data illustrated in FIGS. 4 and 5 is merely exemplary, and other types of signal processing may be used. For example, the cutoff frequencies described above for the high-pass and low-pass filters may be varied, or other filters may be added. Likewise, some or all of the frequency filtering may be performed using analog filters, with the output of these filters sampled, i.e., digitized, separately. Similarly, some or all of the filtering and/or detecting may be done in the processor. Furthermore, the raw accelerometer data may be applied to additional filters to provide data for other purposes. For example, a bandpass filter may be provided, the output of which is used to monitor patient activity.

Figure 8A:
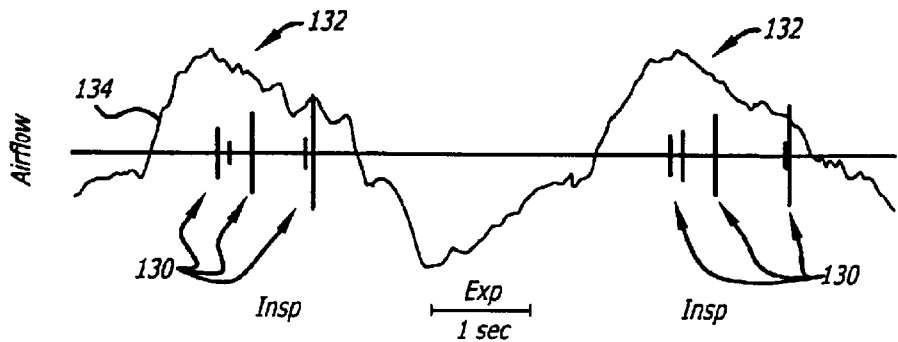
FIGS. 8a–8c are exemplary output waveform displays of various respiratory cycles and adventitious lung sounds detected by the system of FIG. 1
Figure 8B:
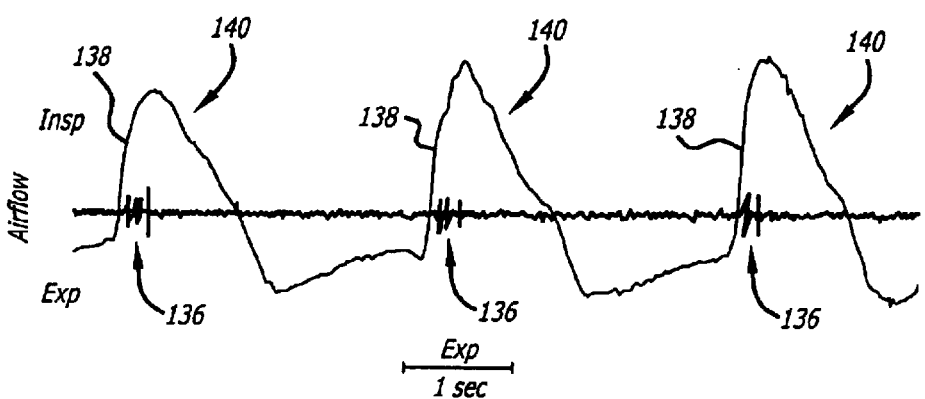
Figure 8C:
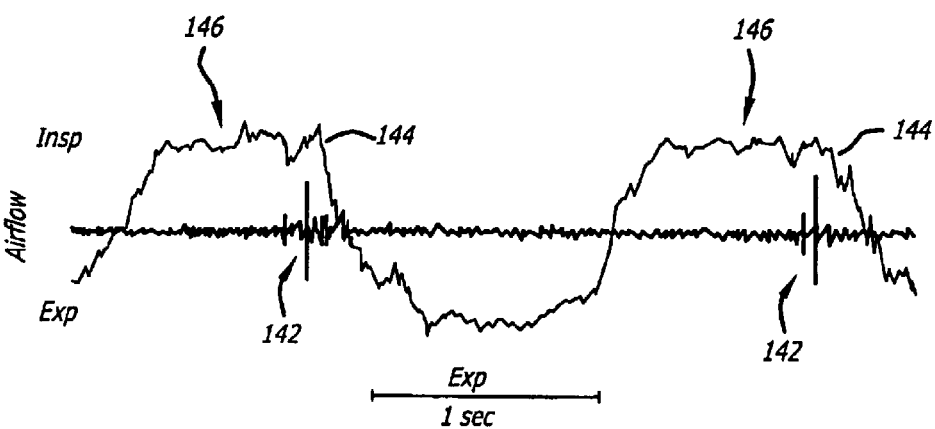

With reference to FIGS. 8a–8c, exemplary visual displays generated by the external device 54 on an output device 62 are shown. In these examples, it is assumed the implantable device 18 includes an accelerometer 36 and a respiratory cycle sensor 43 and that the implantable device 18 transmits the raw sensed signals from each of these sensors to the external device 54. It is also assumed that the external device 54 generates display control signals that are output to a display to generate these outputs. In each of these examples the visual displays of the respiratory cycle and the lung sounds are overlaid or plotted adjacently with a common time axis to show the time relationship between the two. In FIG. 8a, adventitious lung sounds 130 occur throughout each of the inspiratory portions 132 of the respiratory cycle 134. In FIG. 8b, adventitious lung sounds 136 occur throughout the early part 138 of each inspiratory portion 140. In FIG. 8c, adventitious lung sounds 142 occur throughout the late part 144 of each inspiratory portion 146. In FIGS. 8a–8c, airflow curves are shown. Alternatively, a signal representative of lung volume may be presented along with the lung sound signal.

In one embodiment, one or more of the output devices 62 (or the output devices 70) comprises an audio device for generating audio outputs representative of the lung sounds. For example, raw accelerometer data 94 may be applied to a speaker to allow the user to hear and identify lung abnormalities. Alternatively, processed accelerometer data, such as processed accelerometer data 98, maybe applied to an audio device to allow the user to hear and identify lung abnormalities. Other types of processed accelerometer data, including filtered and signal-averaged accelerometer data, may also be applied to an audio device to allow the user to hear and identify lung abnormalities. In each case, the user is presented with the lung sounds in the audio domain, which may be more familiar to a physician or other user who is used to listening to lung sounds using a stethoscope. In each case, the user may also be presented with any or all of the traces shown in FIGS. 8a–8c, such that the user may receive respiratory cycle and lung sound information in both the visual and the audio domains.

In another embodiment, the implantable device 18 includes a pulmonary logbook feature. With this feature the implantable device 18 records data in memory for later examination by a physician for use in making a diagnosis. The implantable device 18 may, for example, continually record data in an area of the memory 34. Alternatively, the device 18 may only record data if adventitious lung sounds are detected. To provide the pulmonary logbook feature, in one embodiment, the controller 32 of the implantable device 18 performs the signal processing previously described with respect to the external device 54 as shown in FIG. 1.

With the logbook feature, on the next visit of the patient to a doctor, the doctor can use an external device 54 to read the data from the logbook and can examine the data to look for rales events. When the controller 32 determines that a rales logbook playback command is received from the external device 54, the controller 32 transmits the records from the memory 34 to the external device. The external device 54 then outputs the data from these records to the output device(s) 62 (or output device(s) 70). The physician can then examine the recorded data to aid in making a diagnosis.

A cause of pulmonary congestion is inadequate pumping of the left side of the heart. In another embodiment of the system, the left side of the heart may be made to pump faster through use of an implantable pulse generator in response to information obtained through analysis of the detected lung sounds. In operation, the pulse generator outputs electrical pulses to either one or more of the atrial and ventricular electrodes 46, 50 in order to stimulate the heart. In this configuration of the system, the output of the pulse generator of the device, i.e., the atrial and ventricular stimulating circuits 28 and 30, is controlled by the controller 32. As previously described, the controller 32 may analyze lung sounds to detect the presence of adventitious lung sounds. In addition, the controller 32 may be programmed to monitor the lung sounds for characteristics or trends indicative of the continuous presence of adventitious lung sounds which serves as an indication of lung congestion. For example, if adventitious lung sounds are continuously detected over a given time period, the controller 32 may cause the pulse generator to increase the frequency of its output to the stimulating electrodes. When adventitious lung sounds are no longer detected over a given period of time, the controller may cause the output of the pulse generator to return to its normal frequency.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A lung sound detection system comprising:
    an implantable sensor adapted to be positioned adjacent to a pulmonary system and to output signals indicative of lung sounds in response to pulmonary system activity; and
    a controller adapted to receive the signals and to process the signals to detect the presence of adventitious lung sounds, wherein the controller is further adapted to filter the signals to remove frequencies unrelated to adventitious lung sounds and compare any remaining signals to a criteria indicative of adventitious lung sounds, and the controller is further adapted to obtain a spectrum analysis of the signals and compare those components of the spectrum analysis indicative of adventitious lung sounds to a threshold intensity.

2. The system of claim 1 wherein the sensor is associated with an implantable device.

3. The system of claim 1 wherein the sensor is a pressure sensor.

4. The system of claim 1 wherein the sensor is a vibration sensor.

5. The system of claim 1 wherein the controller is further adapted to compare any components indicative of adventitious lung sounds to a criteria indicative of the severity of adventitious lung sounds.

6. The system of claim 5 wherein the criteria indicative of the severity of adventitious lung sounds comprises a threshold intensity.

7. The system of claim 5 wherein the criteria indicative of the severity of adventitious lung sounds comprises a time duration.

8. A lung sound detection system comprising:
an implantable sensor adapted to be positioned adjacent to a pulmonary system and to output signals indicative of lung sounds in response to pulmonary system activity; and
a controller adapted to receive the signals and to process the signals to detect the presence of adventitious lung sounds, wherein criteria indicative of adventitious lung sounds comprises a threshold amplitude, and the controller is further adapted to compare any signals indicative of adventitious lung sounds to a criteria indicative of the severity of adventitious lung sounds;
wherein the implantable sensor is an accelerometer.

9. The system of claim 8 wherein the criteria indicative of the severity of adventitious lung sounds comprises a threshold amplitude.

10. The system of claim 8 wherein the criteria indicative of the severity of adventitious lung sounds comprises a time duration.

11. A method of detecting lung sounds comprising:
obtaining signals indicative of lung sounds from an implantable sensor positioned adjacent to a pulmonary system; and
processing the signals to detect the presence of adventitious lung sounds, including obtaining a spectrum analysis of the signals and comparing those components of the spectrum analysis indicative of adventitious lung sounds to a criteria indicative of the severity of adventitious lung sounds.

12. The method of claim 11 wherein the criteria indicative of the severity of adventitious lung sounds comprises a threshold intensity.

13. The method of claim 11 wherein the criteria indicative of the severity of adventitious lung sounds comprises a time duration.

14. A method of applying electrical pulses to a heart comprising:
receiving signals indicative of lung sounds from an implantable sensor adapted to be positioned adjacent to a pulmonary system;
monitoring the lung sound signals for the presence of adventitious lung sounds; and
controlling the output of an implantable pulse generator having at least one stimulating lead positioned within a heart, in response to characteristics of the adventitious lung sounds.

15. A lung sound detection system comprising:
an implantable sensor adapted to be positioned adjacent to a pulmonary system and to output signals indicative of lung sounds in response to pulmonary system activity, wherein the implantable sensor is further adapted to output signals indicative of the posture of the body associated with the pulmonary system; and
a controller adapted to receive the signals and to process the signals to detect the presence of adventitious lung sounds and the posture of the body.

16. The system of claim 15 wherein in order to process the signals, the controller is further adapted to:
filter the signals to remove frequencies unrelated to posture; and
compare any remaining signals to a criteria indicative of a specific posture.

17. A method of detecting lung sounds comprising:
obtaining signals indicative of lung sounds from an implantable sensor positioned adjacent to a pulmonary system;
receiving output signals indicative of the respiratory cycle associated with the pulmonary system from an implantable respiratory sensor;
detecting portions of the respiratory cycle based on the respiratory-cycle signals; and
processing lung-sound signals to detect the presence of adventitious lung sounds only during specific portions of the respiratory cycle.

18. A lung sound detection system comprising:
an implantable sensor adapted to be positioned adjacent to a pulmonary system and to output signals indicative of lung sounds in response to pulmonary system activity;
an implantable respiratory sensor adapted to output signals indicative of the respiratory cycle associated with the pulmonary system; and
a controller adapted to receive the lung sound signals and to process the lung sound signals to detect the presence of adventitious lung sounds, and the controller is further adapted to receive the respiratory-cycle signals, to detect portions of the respiratory cycle based on the respiratory-cycle signals and to process lung-sound signals only during a specific portion of the respiratory cycle.

19. The system of claim 18 wherein the portions of the respiratory cycle comprise an inspiratory portion and an expiratory portion and the controller is adapted to process the lung-sound signals only during the inspiratory portion.

20. The system of claim 19 wherein the inspiratory portion comprises an early portion and a late portion and the controller is further adapted to detect these portions.

21. A method of detecting lung sounds comprising:
obtaining signals indicative of lung sounds from an implantable sensor positioned adjacent to a pulmonary system;
processing the signals to detect the presence of adventitious lung sounds; and
receiving signals indicative of the posture of the body associated with the pulmonary system from an implantable sensor and processing the signals to detect the posture of the body.

22. The method of claim 21 wherein processing the signals comprises:
filtering the signals to remove frequencies unrelated to posture; and
comparing any remaining signals to a criteria indicative of a specific posture.

23. A system for providing data related to the pulmonary system, said system comprising:
an implantable sensor adapted to be positioned adjacent to a pulmonary system and to output signals indicative of sounds;
an implantable respiratory cycle sensor adapted to output signals indicative of the respiratory cycle associated with the pulmonary system; and a controller adapted to receive the sound signals and the respiratory-cycle signals, to generate data representative of the signals and to provide the data to a secondary device, wherein the controller is adapted to filter the sound signals to remove signal components unrelated to the activity of the pulmonary system, and the controller is further adapted to filter the remaining sound signals to remove signal components unrelated to adventitious lung sounds.

24. The system of claim 23 wherein the controller is adapted to detect portions of the respiratory cycle based on the respiratory-cycle signals and to generate and provide data only during a specific portion of the respiratory cycle.

25. The system of claim 23 wherein the controller is adapted to process the respiratory-cycle signals to identify the inspiratory portion of the cycle and to generate and provide data only during the inspiratory portion.

26. The system of claim 23 wherein the secondary device is a display.

27. A method of detecting lung sounds comprising:
obtaining signals indicative of lung sounds from an implantable sensor positioned adjacent to a pulmonary system; and
processing the signals to detect the presence of adventitious lung sounds, including filtering the signals to remove frequencies unrelated to adventitious lung sounds and comparing any signals indicative of adventitious lung sounds to a criteria indicative of the severity of adventitious lung sounds.

28. The method of claim 27 wherein the criteria indicative of the severity of adventitious lung sounds comprises a threshold amplitude.

29. The system of claim 27 wherein the criteria indicative of the severity of adventitious lung sounds comprises a time duration.

30. An implantable system comprising:
an implantable sensor adapted to be positioned adjacent to a pulmonary system and to output signals indicative of lung sounds;
at least one stimulating lead adapted to be positioned within a heart;
a pulse generator adapted to output electrical pulses to the lead; and
a controller adapted to receive the lung-sound signals, to monitor the lung-sound signals for the presence of adventitious lung sounds and to control the output of the pulse generator in response to characteristics of the adventitious lung sounds.

* * * * *